United States Patent

Knepp

[11] Patent Number: 6,056,400
[45] Date of Patent: May 2, 2000

[54] PROTECTIVE EYEWEAR WITH TRANSPARENTLY TINTED VISOR

[75] Inventor: Christine F. Knepp, York, Pa.

[73] Assignee: Yorktowne Optical Company, Inc., Emigsville, Pa.

[21] Appl. No.: 09/208,747

[22] Filed: Dec. 10, 1998

[51] Int. Cl.$^7$ ........................................ G02C 3/00
[52] U.S. Cl. ........................ 351/155; 351/44; 2/12
[58] Field of Search ...................... 351/41, 158, 44, 351/45; 2/12, 446, 448

[56] References Cited

U.S. PATENT DOCUMENTS

| | | |
|---|---|---|
| D. 185,225 | 5/1959 | Moeller . |
| D. 211,413 | 6/1968 | Mitchell . |
| D. 214,258 | 5/1969 | Carpenter et al. . |
| D. 281,507 | 11/1985 | Schremmer . |
| D. 293,328 | 12/1987 | Murphy et al. . |
| D. 293,450 | 12/1987 | Jannard . |
| D. 294,952 | 3/1988 | Wilson . |
| D. 295,286 | 4/1988 | Takeuchi . |
| D. 313,236 | 12/1990 | Mackay . |
| D. 317,771 | 6/1991 | Mackay . |
| D. 335,133 | 4/1993 | Langley . |
| 3,575,497 | 4/1971 | Leblanc . |
| 3,876,295 | 4/1975 | Loughner . |
| 4,047,249 | 9/1977 | Booth . |
| 4,271,538 | 6/1981 | Montesi et al. . |
| 4,386,832 | 6/1983 | Nannini . |
| 4,976,530 | 12/1990 | Mackay et al. . |
| 5,005,214 | 4/1991 | Koethe . |
| 5,335,025 | 8/1994 | Wang . |
| 5,390,369 | 2/1995 | Tubin . |
| 5,519,460 | 5/1996 | Mills . |
| 5,669,071 | 9/1997 | Vu . |

OTHER PUBLICATIONS

Yorktowne Optical Company Incorporated, SOLARSHIELDS promotional material, 1986.
Yorktowne Optical Company Incorporated, SOLARSHIELDS promotional material.
New Equipment Digest, Sep. 1968, p. 92, M–S–A Visitor Goggles.
Hong Kong Enterprise, Jul. 1988, p. 150, Francini frames labelled Nos. 3–5.
Coca Cola Heatwave Sunglasses advertising sheet.

*Primary Examiner*—Hung Xuan Dang
*Attorney, Agent, or Firm*—Nixon Peabody LLP; Charles M. Leedom, Jr.

[57] ABSTRACT

An improved protective eyewear that will provide maximum protection to the wearer from the brightness of the sun and the harmful UV rays, while at the same time, provide maximum utility and appeal at minimal cost to the wearer. In accordance with one embodiment, the protective eyewear is a wrap-around type including a transparently tinted visor attached to a lens support member such that the visor is within the wearer's field of vision and provides protection from the brightness of the sun and the harmful UV rays and maximizes the utility of the protective eyewear. The protective eyewear also minimizes undesirable obstruction of the wearer's field of vision and maximizes the appeal of the protective eyewear at a minimal cost to the wearer.

27 Claims, 2 Drawing Sheets

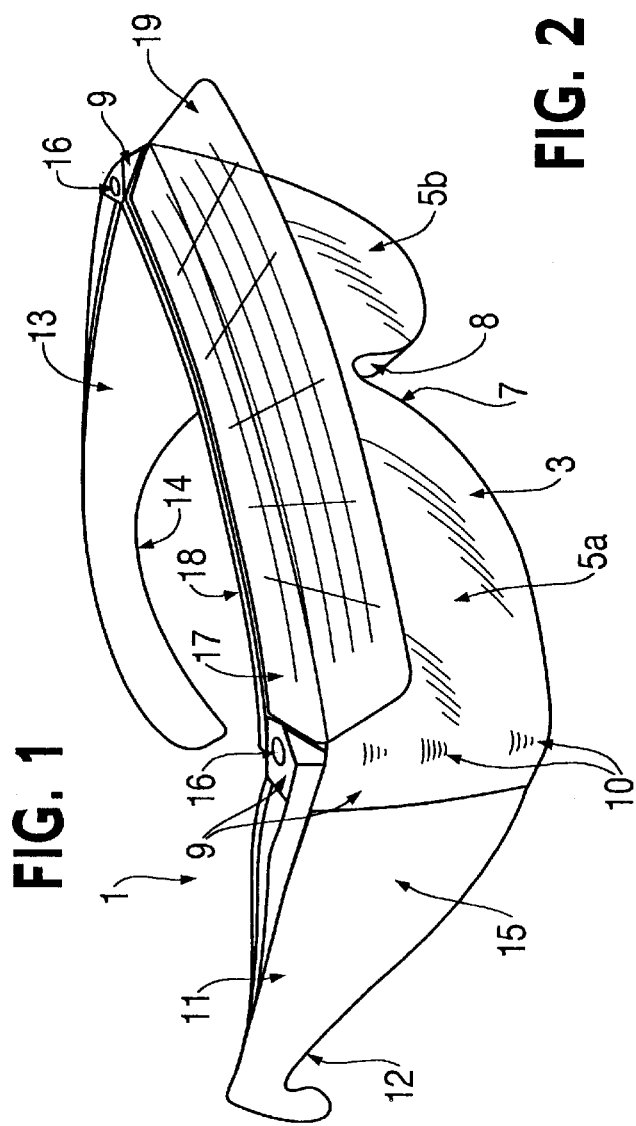
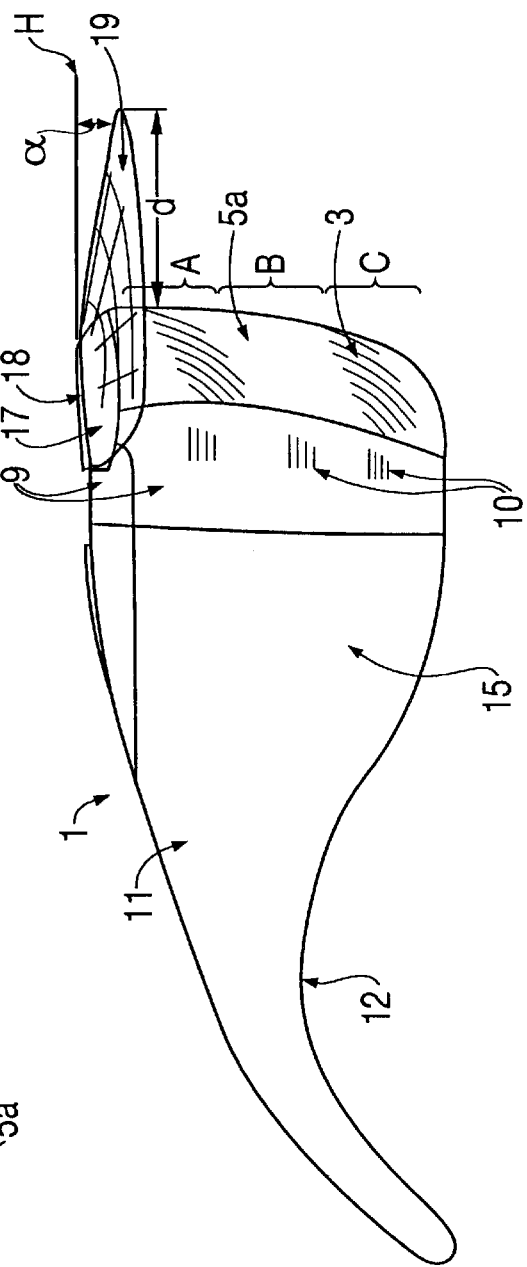

PROTECTIVE EYEWEAR WITH TRANSPARENTLY TINTED VISOR

BACKGROUND OF THE INVENTION

1. Field of the Invention

The present invention is related to the field of glasses. More specifically, the invention relates to protective eyewear including a visor.

2. Description of Related Art

Eyeglasses and sunglasses are generally known in the art and are commonly used to correct vision problems and to provide protection to the eyes, both from air borne objects, and from harmful electromagnetic radiation. Sunglasses and other eyewear designs which are commonly used to protect the eyes from the sun are often manufactured from plastic materials but are still commonly referred to as glasses. Various eyeglass and sunglass designs and accessories have been developed to provide increased protection to the wearer from the brightness of the sun, such designs and accessories including clip-on eye protectors, gradient lenses and visors, including wrap-around type protective eyewear with visors. However, as will be discussed in more detail below, all of these known sunglass and protective eyewear designs and accessories are subject to various limitations which compromise the protection offered to the wearer, limit their utility, substantially reduce the wearer's visibility and/or diminish their aesthetic appeal.

The general features and design of conventional sunglasses is well known in the art and need not be discussed in detail here. It has been recognized in the art that many wearer's of sunglasses must also use prescription glasses to correct various eye conditions such as near-sightedness, far-sightedness and stigmatism. To provide protection from the brightness of the sun and to eliminate the need for a separate pair of prescription sun glasses which are generally very expensive, auxiliary clip-on eye protectors have been designed in various forms for use in conjunction with the prescription glasses. Such clip-on eye protectors are installed directly on the lenses of the prescription glasses and are illustrated in U.S. Pat. No. 3,575,497 to Leblanc and U.S. Pat. No. 3,876,295 to Loughner. The lenses of these clip-on eye protectors may be tinted to provide light protection and may be pivotally moved between an operative position where the lenses cover the lenses of the prescription glasses and an inoperative position out of the line of vision of the wearer. These clip-on protectors are generally provided with a single, uniform tinting and are generally very dark in order to provide adequate protection to the eyes. However, because these clip-on protectors are merely additional lenses in front of the prescription glasses with conventional frame designs, they do not provide any additional protection from the intense light of the sun than do any other conventional sunglasses. More specifically, when conventional sunglasses are worn, there are usually substantial gaps between the wearer's eyes and the dark tinted lenses especially at the side temple region, near the nose support region and near the eye brow region. Because these gaps allow the sun light and air borne objects to enter the eye, conventional sunglasses and glasses utilizing the clip-on protectors do not provide maximum protection to the wearer's eyes thereby compromising the protection to the wearer.

In addition, the very dark tinting has some disadvantages in that wearers have found that the glasses were too dark to wear when the sky is slightly overcast with cloud cover or during dusk when the intensity of the sunlight is reduced. Therefore, in these conditions, the wearer's visibility was through such clip-on protectors is substantially reduced making the use of such protectors not practical under these conditions. In addition, other wearers objected to the very dark tinting even in very bright conditions because it prevented others from being able to make eye contact with the wearer since the wearer's eyes could not be readily seen through the dark tinting. And whereas these clip-on protectors can be placed in their inoperative position, wearers find them to be aesthetically unacceptable in this position and most wearers object to the perceived tacky and gaudy look and the image such look portrays about the wearer.

While these clip-on eye protectors were intended to be only functional in their operative position, the present inventors have found that these clip-on protectors provide some amount of protection to the wearer's eyes when in their inoperative position since intensity of light overhead which reaches the wearer's eyes is reduced by the tinted lenses. However, because the original intended use is as a lens and the clip-on eye protectors include a nose bridge area, the clip-on protectors only provide minimal protection to the wearer's face, especially with respect to the wearer's nose which is known to be more prone to sunburn than any other part of a person's face. And as previously noted, the conventional glasses to which these clip-on eye protectors are attached have been found to be wholly inadequate in providing maximum protection for the wearer's eyes.

Some sunglass designs have attempted to alleviate the disadvantage of dark tinting by providing a gradient lenses in which the tinting is very dark at the top portion of the lens and gradually decrease in darkness toward the bottom portion of the lens. This offered superior protection to the eyes when the wearer's eyes are directed upwardly toward the sun while providing a lighter tinting at the mid portion and the lower portion of the lens such that the sunglasses may still be worn during overcast conditions or during dusk when the intensity of the sun is reduced. Another advantage of the gradient lenses is that they permit eye contact with the wearer through the lighter tinted mid and lower portions of the lens. However, since these gradient lenses are provided on conventional sunglass frames, they also do not provide the maximum protection to the wearer's eyes from the sun light or provide any protection to the wearer's face. In addition, manufacturing of these gradient lenses is very expensive and difficult which makes the use of these gradient lenses impractical and less appealing for many people.

Protective eyewear designs have continued to develop and one design in common use today is the wrap-around design such as those sold under the trademark SOLARSHIELD® as well as WRAP AROUND SUNGLASSES which are distributed and sold by the assignee of this invention. More recent designs of such wrap-around eyewear is disclosed in U.S. Pat. No. D313,236 to Mackay. These wrap-around eyewear designs have been found to offer superior protection to the eyes when compared to conventional eyeglass and sunglass designs since they cover a larger area around the eyes and are generally provided with wide temple portions. More specifically, this additional coverage and the wide temple portions have been found to provide superior physical barrier to objects and projectiles which can enter the eye through the gaps present between the wear's face and conventional sunglasses.

In addition, the wrap-around eyewear of the type described above will often provide additional protection to the wearer by including transparently tinted material capable of filtering out or reducing harmful radiation, such as ultra-violet (UV) radiation while allowing less harmful visible radiation to pass through. Such transparently tinted material may be positioned to be in front of the wearer's eyes and allow an unobstructed forward field of vision while protecting the eyes from harmful radiation. The surrounding portions of the protective eyewear may include similar material or opaque material that completely blocks the entry of light (including harmful radiation) that could otherwise enter the wearer's eyes peripherally or after multiple reflections as occurs when more conventional sunglasses are worn. This shielding effect is accentuated if the temple portions are widened (as compared with conventional eye wear) and are formed of a tinted material capable of reducing the amount of sunlight (especially the harmful radiation) which can enter the eyes through the side gaps of conventional eyeglass designs. Furthermore, these wrap-around eyewear could be designed so that prescription glasses may be worn underneath the wrap-around eyewear thereby allowing the wearer to wear and use the corrective prescription glasses in conjunction with the wrap-around eyewear at a minimal additional cost.

These wrap-around eyewear designs have been especially useful in the medical applications for patients who have undergone cataract surgery and have heightened sensitivity to UV rays and the brightness of the sun. In this regard, the wrap-around protective eyewear have been provided with very dark tinting in order to provide the maximum protection from the brightness of the sun and have been made with materials that block the harmful UV rays. Wearers of such wrap-around protective eyewear have found that the very dark tinting provided ample protection from the sun, especially when the sun is very bright. However, like the wearers of the clip-on eye protectors, these wearers have also found that the wrap-around protective eyewear were too dark when the intensity of the sunlight is reduced and found that the dark tinting substantially reduced the visibility of the wearer in these conditions. In addition, wearers objected to the very dark tinting because it prevented others from being able to make eye contact with the wearer. Furthermore, use of gradient lenses was found to be impractical because of the high manufacturing costs and too expensive for many people. This impracticability is heightened by the fact that many of the wearers of such wrap-around sunglasses purchase them solely for post-eye surgery use, do not want to spend a large amount of money for temporary glasses.

More recently, eyeglasses and sunglasses including an opaque visor on the upper portion of the glass frame has been developed and is illustrated in U.S. Pat. No. 5,005,214 to Koethe. These designs include a removably attached visor on the front frame section of an eyeglass that provides additional shading to the wearer's face such as to the wearer's nose which is susceptible to sunburns. As illustrated in U.S. Pat. No. 4,976,530 to Mackay et al., U.S. Pat. No. 5,390,369 to Tubin and U.S. Pat. No. D294,952 to Wilson, wrap-around eyewear with opaque visors have also been designed and are known in the art. These sunglasses have been designed to combine the benefits of providing additional shading to the wearer's face while also providing better eye protection offered by the wrap-around type eyewear designs as discussed above.

Although the wrap-around eyewear designs which include an opaque visor such as those disclosed in the above noted Mackay and Tubin references provide most of the benefits of the wrap-around design discussed previously and have also been found to provide additional shading to the wearer's face, deficiencies have also been found in these designs as well. For instance, it has been found that these designs obstruct the wearer's field of vision at certain angles. As an example, these opaque visor designs prevent the wearer from seeing objects which are somewhat overhead such as road signs and traffic lights at an intersection. Correspondingly, the utility of these sunglass designs with visors is greatly diminished since they cannot be safely used while driving a motor vehicle or in other situations which require unobstructed field of vision of the wearer. In addition, many wearers found that these wrap-around eyewear with opaque visors induces an "enclosed" or "boxed-in" feeling which is caused by the opaque visor limiting the wearer's field of vision. When these limitations are combined with the disadvantages of the previously discussed wrap-around eyewear designs of the prior art such as the very dark tinting and reduced aesthetic appeal, the utility and appeal of such eyewear is greatly diminished.

Therefore, there exists an unfulfilled need for a protective eyewear design that will provide maximum protection to the wearer from the brightness of the sun and the harmful UV rays and maximize the utility of the protective eyewear, while at the same time, minimizing undesirable obstruction of the wearer's field of vision and maximizing the appeal of the protective eyewear at a minimal cost to the wearer.

SUMMARY OF THE INVENTION

In view of the foregoing, it is an object of the present invention to provide an improved protective eyewear that offers maximum protection from the sun and from harmful radiation to the wearer's eyes and face by providing a visor on the protective eyewear.

A second object of the present invention is to provide an improved protective eyewear which maximizes the utility of the protective eyewear such that the wearer can use the protective eyewear with a transparently tinted visor in activities where other glasses with prior art opaque visors cannot be safely used.

A third object of the present invention is to provide an improved protective eyewear including a transparently tinted visor which minimizes undesirable obstruction of the wearer's field of vision thereby further maximizing utility and appeal of the protective eyewear.

Another object of the present invention is to provide an improved protective eyewear which is both functionally and aesthetically appealing to the wearer by providing a lighter tinted lens than conventional sunglasses while at the same time, maintaining maximum protection from the brightness and harmful ultra-violet rays of the sun by providing a visor which is transparently tinted.

Yet another object of the present invention is to provide an improved protective eyewear including a transparently tinted visor which is polarized to block horizontal light waves thereby reducing glare to the wearer.

Still further, it is an object of the present invention to provide an improved protective eyewear that accomplishes these above objectives economically by minimizing costs.

In accordance with one embodiment of the present invention, these objects are obtained by an improved protective eyewear for maximizing protection against harmful radiation while minimizing obstruction of a wearer's visual acuity comprising a lens including a transparently tinted optical area positioned in front of an eye of the wearer in a manner that the lens is positioned within the wearer's forward field of vision, a lens support including an upper surface, first and second temporal members hingedly attached to the ends of the protective eyewear, and a transparently tinted visor attached to the upper surface of the lens support. The transparently tinted visor extends substantially continuously across the lateral length of the protective eyewear and reduces the intensity of light transmitted through the transparently tinted visor thereby providing shading to the wearer's eyes and face from the sun and other overhead lighting. The transparently tinted visor may be attached to the upper surface at a slight downward angle such that when the protective eyewear is worn, the transparently tinted visor extends into the wearer's field of vision and objects are viewable through both the lens and the transparently tinted visor. In one embodiment, the luminous transmittance is reduced to between 5 and 25 percent when objects are viewed through both said lens and said transparently tinted visor. In another embodiment both the lens of the protective eyewear and the transparently tinted visor may have a transmittance of substantially 35 percent in the visible spectral region of light, and be formed of a material that blocks substantially all of ultra-violet spectral region of light. The visor and the lens may be designed in conjunction with each other with a traffic signal transmittance of substantially 35 percent in the spectral wavelength range between 500 and 650 nanometers thereby allowing the wearer to use the protective eyewear while driving and to recognize the traffic lights. The transparently tinted visor may also be made from a polarized material with polarizance of at least 90 percent which blocks horizontal light waves to provide further protection to the wearer from horizontally reflected glare.

These and other objects, features and advantages of the present invention will become more apparent from the following detailed description of one embodiment of the present invention when viewed in conjunction with the accompanying drawings.

BRIEF DESCRIPTION OF THE DRAWINGS

FIG. 1 is a panoramic perspective view of an improved protective eyewear in accordance with one embodiment of the present invention.

FIG. 2 is a side profile view of the protective eyewear illustrated in FIG. 1.

DETAILED DESCRIPTION OF THE PREFERRED EMBODIMENTS

Figure 3A:
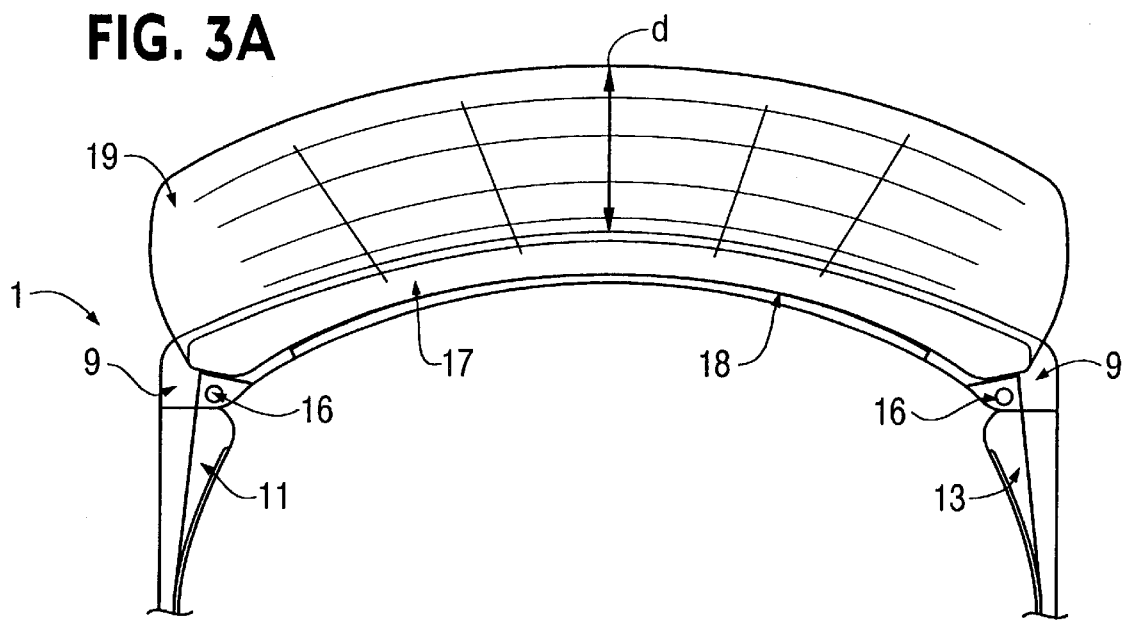
FIG. 3A is a topographical view of the transparently tinted visor used in the protective eyewear illustrated in FIG. 1 and FIG. 2.

FIG. 1 illustrates an improved protective eyewear 1 in accordance with one embodiment of the present invention that provides maximum protection to the wearer from the brightness of the sun and the harmful UV rays. As will be further discussed below, the protective eyewear 1 maximizes its utility for the wearer, while at the same time, minimizing undesirable obstruction of the wearer's field of vision. The present invention also maximizes the appeal of the protective eyewear at a minimal cost to the wearer thereby fulfilling the present need for such eyewear. As illustrated in FIG. 1, the protective eyewear 1 is of the wrap-around type eyewear generally known in the art. However, the present invention may also be practiced in other eyewear such as conventional eyeglasses and sunglasses as well as in other eyewear designs.

The protective eyewear 1 is provided with a lens 3 which includes transparently tinted optical areas 5a and 5b positioned in front of the eyes of the wearer within the wearer's forward field of vision. The lens 3 which includes the optical areas, may be made of various materials already known in the art including glass and plastic, and may be designed to provide protection from harmful electromagnetic waves such as the harmful UV rays of the sun. Of course, because the illustrated embodiment is a wrap-around type eyewear, the lens 3 may be formed from a single, unitary piece with the optical areas 5a and 5b integrally formed thereon. However, in other embodiments of the present invention as applied to other eyewear designs, the lens may be formed from multiple and/or separate pieces as know in the art.

The lens 3 includes a recessed nose area 7 including a nose support 8 (only one shown) which allows the protective eyewear 1 to be supported on the wearer's face (not shown) in the manner conventionally known in the art. An integral lens support portion 9 is provided on the protective eyewear 1 for supporting the lens 3 in the desired position within the wearer's forward field of vision. As illustrated in the figure, the lens support portion 9 of the present embodiment is integrally formed on the lens 3 from a similar transparently tinted material so as to allow the wearer to see objects through the lens support portion. It is also noted that because the lens support portion 9 is integrally formed with the lens 3 in the illustrated embodiment, a curved portion 10 is present where the lens 3 transitions into the support portion 9. The plurality of short parallel lines which depict the curved portion 10 are shown for illustrative purposes only and do not represent any structural features in particular.

The protective eyewear 1 also includes a first temporal member 11 attached to the lens support portion 9 on one end of the protective eyewear 1 and a second temporal member 12 attached to the lens support portion 9 on another end of the protective eyewear 1. These temporal members allow the protective eyewear 1 to be worn by the wearer in a manner conventionally known in the art. In this regard, both the first temporal member 11 and the second temporal member 12 may be provided with ear receiving portions 12 and 14 respectively which is curved to receive the top portions of the wearer's ears thereby retaining the protective eyewear 1 in position on the wearer's face. In this embodiment, each of the temporal members 11 and 12 may also include a wide temple portion 15 that is commonly used in wrap-around eyewear designs and which provides additional protection from airborne objects and projectiles as discussed previously. Furthermore, the temporal members 11 and 12 and/or the wide temple portion 15 may be made from a similar tinted material as the lens 3 thereby allowing the wearer to have peripheral vision through the temporal members while at the same time, providing protection from intense light and harmful radiation such as UV rays. To increase utility and portability, the first and second temporal members 11 and 13 may be hingedly attached by integral hinges 16 to the lens support portion 9 thereby allowing the temporal members to be folded so as to make the protective eyewear 1 more compact.

In the present embodiment, the lens support portion 9 of the protective eyewear 1 may also include an upper surface 17 which provides a surface on which a transparently tinted visor 19 may be attached. The upper surface 17 of the present embodiment is made from a similar tinted material as the lens 3 and may be integrally formed therewith. In addition, this upper surface 17 may be designed to serve a dual function in that by extending the depth of the surface, the distance between the lens 3 and the wearer's eyes may be increased thereby allowing the wearer to wear prescription glasses underneath the protective eyewear.

The transparently tinted visor 19 which is attached to the upper surface 17 extends substantially continuously across the lateral length of the protective eyewear 1 and is tinted to reduce the intensity of light transmitted through the visor thereby providing shading to the wearer's eyes and face from the sun and other overhead lighting. It is important to note that unlike the opaque visors used in the prior art eyewear designs, the transparently tinted visor 19 in accordance with the present invention is transparent such that the wearer can clearly see objects through the visor. This feature of the invention is clearly illustrated in the figure by the fact that the lens 3 is visible through the visor 19. The web-like cross-hatch on the transparently tinted visor 19 is provided in the figures for illustrative purpose only to show the general surface of the visor and do not represent any structural features in particular.

The protective eyewear 1 is illustrated in FIG. 2 as seen from the side profile view and as illustrated, the transparently tinted visor 19 may be attached to the upper surface 17 at a slight downward angle "$\alpha$" from a horizontal plane "H" and extends distance "d" from the lens 3 such that when the protective eyewear 1 is worn, the transparently tinted visor 19 extends into the wearer's field of vision. Because objects are viewable through both the lens 3 and the transparently tinted visor 19 which extends into the wearer's field of vision, a dual tinting effect is created such that the wearer's field of vision through an upper portion of the lens 3 (generally indicated as "A") is tinted darker than the wearer's field of vision through a mid portion and a lower portion (generally indicated as "B" and "C" respectively) of the lens 3. In this manner, the protective eyewear 1 protects the wearer's eyes from the intensity of the sun while also allowing the lens 3 to have a lighter in tinting than conventional sunglasses and other wrap-around protective eye wear of the prior art. This lighter tinting of the lens 3 and the transparently tinted visor 19 eliminates many of the disadvantages and limitations of the prior art eyewear thereby attaining all the objective set forth previously. More specifically, because the wearer can see through both the lens 3 and the visor 19, obstructions to the wearer's visibility is minimized. The lighter tinted lens 3 also improves the wearer's visibility thereby allowing the protective eyewear 1 to be used in reduced lighting conditions such as during overcast conditions or dusk, while at the same time, providing maximum protection to the wearer's eyes and face when the intensity of the sun and its harmful radiation is the greatest such as when the sun is overhead. This unique design also allows eye contact with the wearer's eyes through the mid portion B and lower portion C of the lens 3 and minimizes the "enclosed" or "boxed-in" feeling thereby improving the appeal of the protective eyewear 1. This dual tinting effect is also created while avoiding the expensive cost of using gradient lenses, thus allowing the protective eyewear 1 to be manufactured and sold inexpensively thereby further improving its appeal.

To provide the desirable facial shading and the dual tinting effect, it is important to carefully select the angle $\alpha$, distance d and the luminous transmittance (or amount of tinting) of the lens 3 and the transparently tinted visor 19. In this regard, an angle $\alpha$ of approximately 10 degrees has been found to be very effective in creating the dual tinting effect and providing the additional protection to the eyes and the face, especially when the sun is overhead and the intensity of the harmful rays is the highest. However, the angle may also be designed to be between 1 to 30 degrees so that the portion of the lens which is provided with a darker tint can be designed in accordance with the desired effect on the wearer's field of vision. For example, the angle a may be increased from 10 degrees to provide a darker tint to a part or all of the mid portion B, or alternatively, the angle $\alpha$ may be decreased to provide a darker tint to only the upper most part of the upper portion A, and so forth. Care must be taken in the selection of the angle $\alpha$ because if the angle a is too large, the transparently tinted visor 19 will not provide the facial protection required and may even provide a darker tint to too much of the wearer's field of vision.

To effectuate the designed angle $\alpha$, the upper surface 17 on the lens support portion 9 may be integrally formed at the desired angle $\alpha$ thereby simplifying the process of attaching the transparently tinted visor 19 on to the upper surface 17. In order to facilitate assembly in the present embodiment, the upper surface 17 of the lens support portion 9 may include a recessed portion or alternatively, an elevated portion 18 for abutting contact with the transparently tinted visor 19. In addition, whereas the transparently tinted visor 19 illustrated in the present embodiment is attached to the upper surface 17 by using an adhesive, other commonly known attaching means may be used (such as fasteners) or provisions may be made for a snap fit assembly. Furthermore, the transparently tinted visor 19 may even be attached to the upper surface 17 by being integrally formed together with the lens support portion 9 or even the lens 3 itself.

Moreover, the transparently tinted visor 19 extends substantially continuously across the lateral length of the protective eyewear 1 and in the present embodiment, may extend horizontally forward from a front surface of the lens 3 at a substantially instant distance d. A distance d of approximately 1.25 inches has been found to be effective in providing protection to the wearer's face and at the same time, providing a dual tinting effect to the upper portion A of the lens 3. However, the transparently tinted visor 19 may extended from the front surface of lens 3 a different distance d depending on the amount of facial shading and the amount of dual tinting effect desired. More specifically, distance d between 0.75 to 2.0 inches has also been found to be effective in providing protection to the wearer's face while creating a dual tinting effect. And as the transparently tinted visor 19 is extended further by increasing distance d, the amount of facial shading provided is increased and the darker tinted area extends further into the mid portion B of the wearer's field of vision. Conversely, as the distance d is reduced, the amount of facial shading provided is also reduced and the darker tinted area is reduced further toward the upper most part of the upper portion A of the lens 3.

It should now be evident from the above discussion that the amount of facial shading provided and the dual tinting effect created by the transparently tinted visor 19 are both controlled by the angle $\alpha$ and the distance d which are somewhat interdependent upon one another such that the design of one may effect the design of the other. Because of this interdependency, the angle $\alpha$ and the distance d may be selected in a complementary fashion to optimize the facial shading provided and the dual tinting effect created in accordance with the application and the wearer's needs. For instance, in applications where a greater facial shading is desired, the distance d may be extended and the angle $\alpha$ may be reduced to provide a particular dual tinting effect. Still in other applications, the converse may apply so that as the distance d is reduced and the angle $\alpha$ may be increased to provide a similar dual tinting effect. Optimal designs for a particular application may be attained by initially selecting the distance d to provide a predetermined amount of the facial shading and then selecting the angle $\alpha$ to provide the desired dual tinting effect. In this manner, the interdependent angle $\alpha$ and distance d of the transparently tinted visor 19 may be designed to precisely control of the amount of facial shading provided and the dual tinting effect created.

In addition to the above dimensional considerations, it is important to carefully select the luminous transmittance (or amount of tinting) of the lens 3 and the transparently tinted visor 19. This careful selection is very important because the lens 3 and the transparently tinted visor 19 act in conjunction with each other to provide the desired dual tinting effect and to protect the wearer's eyes and face. Consequently, the chosen luminous transmittance of one can restrict the choice of luminous transmittance of the other in certain applications. In the present embodiment, luminous transmittance of 12 percent in the visible spectral region when objects are viewed through both the lens 3 and the transparently tinted visor 19 in the upper portion A of the lens 3, has been found to be very effective in creating the desired dual tinting effect and visibility while maintaining protection to the wearer's eyes and face. However, the luminous transmittance of between 5 and 25 percent in the visible spectral region have also been found effective in providing adequate visibility and protection to the wearer. In this regard, it should be noted that ANSI Z80.3-1996 standards applicable to sunglasses presently require the minimum luminous transmittance to be at least 8 percent. However, such requirements are subject to change or modified in accordance with additional findings and as different applications for protective eyewear arise. Thus, the present invention with luminous transmittance of between 5 and 8 percent may become practicable at a later time.

With respect to the present embodiment, both the lens 3 and the transparently tinted visor 19 may be tinted to have a luminous transmittance of 35 percent in the visible spectral region of light, and also designed to block the transmittance of substantially all of ultra-violet spectral region of light. This chosen luminous transmittance has been found to provide optimal visibility to the wearer under conditions when the intensity of the sun is reduced and has also been found to offer protection to the eyes and face of the wearer. In order to maximize the utility of the protective eyewear 1, both the lens 3 and the transparently tinted visor 19 may have a traffic signal transmittance of substantially 35 percent in the spectral wavelength range between 500 and 650 nanometers. This allows the wear to distinguish and recognize the various colors of a traffic signal thereby allowing the protective eyewear 1 to be used while operating a motorized vehicle. Of course, it should be recognized that the lens 3 and/or the transparently tinted visor 19 may be designed to have other luminous transmittance values depending upon the desired degree of tinting. However, it has been found that the above described design provided a very effective and appealing protective eyewear 1. In this regard, it should be noted that because the luminous transmittance values of the lens 3 and the transparently tinted visor 19 may be made to be substantially similar (35 percent in the present embodiment), the darkness of the tinting of both the lens 3 and the visor will also substantially the similar in such instance. This ensures that the look of the protective eyewear 1 is harmonious and continuous thereby improving its aesthetic appeal to the wearer.

In addition to the above, the transparently tinted visor 19 in accordance with one embodiment of the present invention may be made from a polarized material with polarizance of at least 90 percent which blocks horizontal light waves. This further adds utility and protects the eyes of the wearer by reducing any potential glare which may be perceived by the wearer through the upper portion A of the lens 3 such as glare reflecting off a surface. For example, perceived glare of the sun reflected off mirrored or glass buildings can be further reduced by providing a transparently tinted visor 19 formed from a polarized material. In another example, when the wearer tilts his or her head (such as during a golf swing), the polarized visor can further reduce the glare off any surface water (such as a lake or a ocean).

FIG. 3A illustrates a topographical view of a portion of the protective eyewear 1 when worn by a wearer (not shown). Again, it is noted that the web-like cross-hatch on the transparently tinted visor 19 is provided for illustrative purpose only and do not represent any structural features in particular. The figure illustrates the general shape of the transparently tinted visor 19 in accordance with the embodiment of the present invention discussed above where the transparently tinted visor 19 extends substantially continuously across the lateral length of the protective eyewear 1. As previously noted, the visor may extend from the front surface of the lens 3 at a substantially constant distance d of approximately 1.25 inches as illustrated. However, distance d between 0.75 to 2.0 inches has also been found to be effective in providing protection to the wearer's face while creating a dual tinting effect to the upper portion A of the lens 3.

Figure 3B:
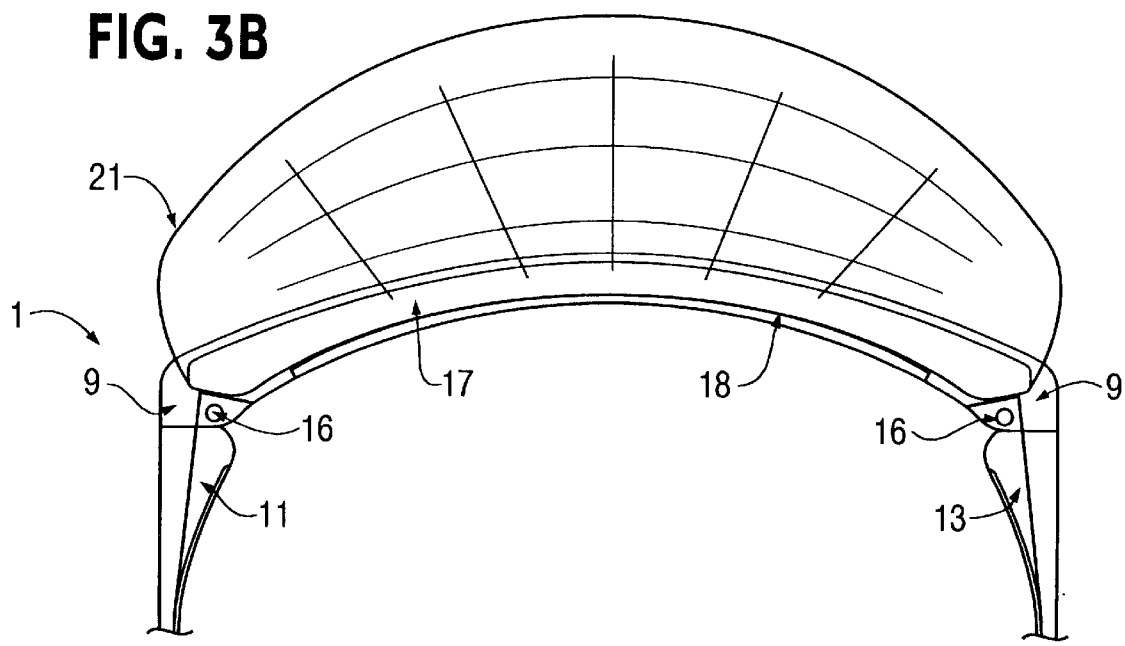
FIG. 3B is a topographical view of an alternative embodiment of a transparently tinted visor in accordance with the present invention.

In addition, FIG. 3B illustrates an alternative embodiment of a transparently tinted visor 21 where the mid-section of the visor extends out further than the end sections such that the visor has an arch shape. Again, it is noted that the web-like cross-hatch on the transparently tinted visor 21 is provided for illustrative purpose only. The arch shape of the transparently tinted visor 21 provides increased facial protection from the sun at the mid-section where the wearer's nose will be positioned thereby further ensuring facial UV protection from the sun. The arch shape also creates a unique dual tinting effect where the darker tinting is provided in a parabolic shape extending toward the middle part of wearer's field of vision. Of course FIG. 3A and FIG. 3B are only illustrative of two embodiments of the present invention. Other shapes and designs of the protective eyewear and transparently tinted visor may be created in accordance with the present invention to provide the desired dual tinting effect and the desired level of protection.

From the foregoing, it should now be apparent how the present invention provides an improved protective eyewear design that will provide maximum protection to the wearer from the brightness of the sun and the harmful UV rays and will maximize the utility of the protective eyewear. Furthermore, it can be seen how the present invention minimizes undesirable obstruction of the wearer's field of vision while maximizing the appeal of the protective eyewear at a minimal cost to the wearer.

What is claimed is:

1. Protective eyewear for maximizing protection against harmful radiation while minimizing obstruction of a wearer's visual acuity comprising:

a lens including a transparently tinted optical area, said lens being positioned in front of an eye of said wearer within said wearer's field of vision;

a support means for supporting said lens in said position in front of the wearer's eye, said support means including an upper surface;

a first temporal member hingedly attached to an end of said protective eyewear;

a second temporal member hingedly attached to another end of said protective eyewear; and a transparently tinted visor attached to said upper surface of said support means and extending substantially continuously across a lateral length of said protective eyewear, said transparently tinted visor allowing light to be transmitted therethrough in a manner that objects are visible through said transparently tinted visor while reducing the intensity of light transmitted through said transparently tinted visor thereby providing shading to said wearer's eyes and face.

2. Protective eyewear of claim 1, wherein said transparently tinted visor is attached to said upper surface in a manner that when said protective eyewear is worn, said transparently tinted visor extends into said wearer's field of vision.

3. Protective eyewear of claim 2, wherein objects are visible to said wearer when viewed through both said lens and said transparently tinted visor.

4. Protective eyewear of claim 3, wherein luminous transmittance is reduced to between 5 and 25 percent when objects are viewed through both said lens and said transparently tinted visor.

5. Protective eyewear of claim 4, wherein said transparently tinted visor has a luminous transmittance of substantially 35 percent in the visible spectral region of light.

6. Protective eyewear of claim 5, wherein said transparently tinted visor also blocks the transmittance of substantially all of ultra-violet spectral region of light.

7. Protective eyewear of claim 6, wherein said transparently tinted visor has a traffic signal transmittance of substantially 35 percent in the spectral wavelength range between 500 and 650 nanometers.

8. Protective eyewear of claim 3, wherein said transparently tinted visor is a polarized visor.

9. Protective eyewear of claim 8, wherein said polarized visor blocks horizontal light waves.

10. Protective eyewear of claim 9, wherein said polarized visor has a polarizance of at least 90 percent.

11. Protective eyewear of claim 3, wherein said transparently tinted visor extends forwardly a horizontal distance from a front surface of said lens at a substantially constant distance across a horizontal length of said transparently tinted visor between said first and second temporal member.

12. Protective eyewear of claim 11, wherein said transparently tinted visor extends forwardly said horizontal distance between 0.75 to 2.0 inches.

13. Protective eyewear of claim 3, wherein said transparently tinted visor extends horizontally forward from a front surface of said lens in an arc across a horizontal length of said transparently tinted visor between said first and second temporal member.

14. Protective eyewear of claim 3, wherein said transparently tinted visor is attached to said upper surface at an angle from a horizontal plane.

15. Protective eyewear of claim 14, wherein said transparently tinted visor is angled downwardly between 1 to 30 degree angle from said horizontal plane.

16. Protective eyewear of claim 15, wherein said upper surface of said support means is sloped downwardly at an angle from a horizontal plane.

17. Protective eyewear of claim 16, wherein said upper surface of said support means includes a recess for receiving said transparently tinted visor.

18. Protective eyewear of claim 16, wherein said upper surface includes an elevated portion for abutting contact with said transparently tinted visor.

19. Protective eyewear for maximizing protection against harmful radiation while minimizing obstruction of a wearer's visual acuity comprising:

a lens including a transparently tinted optical area extending across a wearer's field of vision and an upper lens surface;

a first temporal member hingedly attached to an end of said protective eyewear;

a right temporal member hingedly attached to another end of said protective eyewear; and a transparently tinted visor which allows light to be transmitted therethrough in a manner that objects are visible through said transparently tinted visor, said transparently tinted visor being attached to said upper lens surface such that said transparently tinted visor extends into said wearer's field of vision in a manner to create a dual tinting effect wherein said wearer's field of vision through an upper portion of said lens is tinted darker than said wearer's field of vision through a mid portion and a lower portion of said lens.

20. Protective eyewear of claim 19, wherein luminous transmittance is reduced to between 5 and 25 percent when objects are viewed through both said lens and said transparently tinted visor at said upper portion of said lens.

21. Protective eyewear of claim 20, wherein said transparently tinted visor has a luminous transmittance of substantially 35 percent in the visible spectral region of light.

22. Protective eyewear of claim 21, wherein said transparently tinted visor has a traffic signal transmittance of substantially 35 percent in the spectral wavelength range between 500 and 650 nanometers.

23. Protective eyewear of claim 22, wherein said transparently tinted visor is made from a polarizing material.

24. Protective eyewear of claim 23, wherein said polarizing material blocks the transmittance of substantially all of ultra-violet spectral region of light.

25. Protective eyewear of claim 19, wherein said transparently tinted visor extends forwardly a horizontal distance from a front surface of said lens across a horizontal length of said transparently tinted visor between said first and second temporal member.

26. Protective eyewear of claim 25, wherein said transparently tinted visor is attached to said upper surface at an angle with respect to a horizontal plane.

27. Protective eyewear of claim 26, wherein amount of said dual tinting effect is determined by said angle and said horizontal distance of said transparently tinted visor.

* * * * *